United States Patent
Kim et al.

(10) Patent No.: US 8,557,811 B2
(45) Date of Patent: Oct. 15, 2013

(54) DUAL-COLOR IMAGING METHOD OF SODIUM/CALCIUM ACTIVITIES USING TWO-PHOTON FLUORESCENT PROBES AND PREPARATION METHOD OF TWO-PHOTON FLUORESCENT PROBES

(75) Inventors: Hwan Myung Kim, Gyeonggi-do (KR); Bong Rae Cho, Seoul (KR)

(73) Assignee: Ajou University Industry—Academic Cooperation Foundation, Gyeonggi-do (KR)

( * ) Notice: Subject to any disclaimer, the term of this patent is extended or adjusted under 35 U.S.C. 154(b) by 323 days.

(21) Appl. No.: 12/913,378

(22) Filed: Oct. 27, 2010

(65) Prior Publication Data
US 2012/0035360 A1    Feb. 9, 2012

(30) Foreign Application Priority Data
Aug. 5, 2010   (KR) .......................... 10-2010-0075718

(51) Int. Cl.
*A61K 31/5375* (2006.01)
*A61K 31/5377* (2006.01)
*C07D 417/12* (2006.01)

(52) U.S. Cl.
USPC ........................................ 514/233.8; 544/137

(58) Field of Classification Search
None
See application file for complete search history.

(56) References Cited

PUBLICATIONS

Kim. Angewandte CHemie International Edition, 2010, 49, 6786-89.*
Two-Photon Fluorescent Probes for $Na^+/Ca^{2+}$ Activities In Vivo; The 105th National Meeting of the Korean Chemical Society; Published Apr. 29, 2010, 1 page, Hwan Kim.

* cited by examiner

*Primary Examiner* — Noble Jarrell
(74) *Attorney, Agent, or Firm* — Alston & Bird LLP

(57) ABSTRACT

Provided are a method for dual-color imaging of sodium/calcium activities using a two-photon fluorescent probe and a method for preparing the two-photon fluorescent probe. The disclosed two-photon fluorescent probe for detecting calcium ions near the cell membrane reacts with calcium cations to exhibit strong two-photon fluorescence and may be selectively and easily loaded into the cell membrane by forming a complex with a calcium ion. Further, it allows imaging of the distribution of calcium cations in a living cell or tissue since it can selectively detect calcium ions in the living cell or tissue at a depth of 100 to 200 μm for more than 60 minutes. In addition, by staining the living cell or tissue with two probes of different fluorescent colors, the calcium and sodium activities can be imaged simultaneously at different channels.

7 Claims, 14 Drawing Sheets

DUAL-COLOR IMAGING METHOD OF SODIUM/CALCIUM ACTIVITIES USING TWO-PHOTON FLUORESCENT PROBES AND PREPARATION METHOD OF TWO-PHOTON FLUORESCENT PROBES

CROSS-REFERENCE TO RELATED APPLICATIONS

This application claims priority under 35 U.S.C. §119 to Korean Patent Application No. 10-2010-0075718, filed on Aug. 5, 2010, in the Korean Intellectual Property Office, the disclosure of which is incorporated herein by reference in its entirety.

TECHNICAL FIELD

The present disclosure relates to a method for dual-color imaging of sodium/calcium activities using a two-photon fluorescent probe and a method for preparing the two-photon fluorescent probe. Particularly, the disclosure relates to a two-photon fluorescent probe capable of imaging calcium ion activity near ion channels of the cell membrane with high sensitivity and selectivity and a method for dual-color imaging of exchange and activities of sodium/calcium cations in cells or tissues by staining along with a two-photon sodium probe of another fluorescent color.

BACKGROUND

The change in calcium ion distribution in cells is very important in the study of physiological and pathological phenomena. The calcium ion level in the cell is controlled by pumps or channels existing on the plasma membrane depending on various situations. The concentration of calcium ion is much higher near the cell membrane than its average value in the cell. Depending on physiological activity, it increases up to 100 μM or above. The highly concentrated calcium ions near the cell membrane are known to play important roles in exocytosis of hormones and neurotransmitters, as second messengers in signal transduction, or the like.

A typical mechanism of controlling the concentration of calcium ions is the $Na^+/Ca^{2+}$ exchanger (NCX). When the concentration of calcium ions in a cell increases, the NCX sends the calcium ions out of the cell in exchange for the import of sodium ions in order to maintain homeostasis. This process is called the $Na^+/Ca^{2+}$ exchange.

In order to study this phenomenon, a number of one-photon fluorescent probes have been developed. However, there is no case of imaging the two ions at the same time to study their interactions. Further, since most one-photon probes are problematic in that they have short extraction wavelengths (<500 nm), which limit application to tissue imaging because of shallow penetration depth (<100 μm), photobleaching and cellular autofluorescence.

An ideal solution to this problem is the two-photon microscopy (TPM) wherein two near infrared photons of low energy are used for excitation. The TPM allows a sustained imaging of intact tissue with minimum interference from tissue preparation artifacts that can extend more than 70 μm into the tissue slice. However, until now, there has not been developed a two-photon fluorescent probe capable of imaging the distribution of calcium ions near the cell membrane and sodium ions deep inside the living tissue (>100 μm) at the same time.

SUMMARY

The present disclosure is directed to providing a two-photon fluorescent probe capable of selectively staining the cell membrane and adequate for imaging selectivity and activity of calcium ions near the cell membrane while having a small molecular weight.

The present disclosure is also directed to providing a method for selectively imaging the distribution of calcium ions near the cell membrane in a living cell or tissue using the two-photon fluorescent probe.

The present disclosure is also directed to providing a method for imaging $Na^+/Ca^{2+}$ exchange in a living cell or tissue using the two-photon fluorescent probe and another two-photon fluorescent sodium probe.

The present disclosure is also directed to providing a method for preparing the two-photon fluorescent probe for detecting calcium ions near the cell membrane.

In one general aspect, the present disclosure provides a two-photon fluorescent probe represented by Chemical Formula 1:

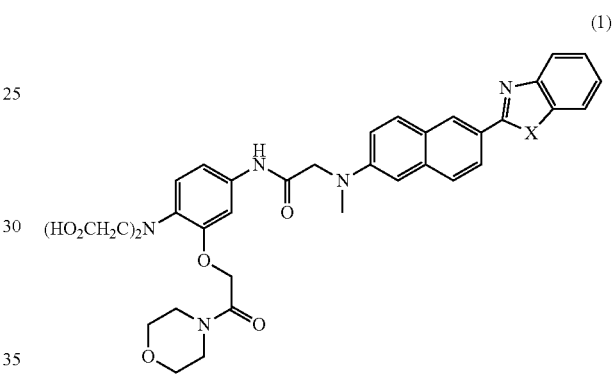

(1)

wherein X is O, S or NH.

In another general aspect, the present disclosure provides a method for preparing a two-photon fluorescent probe represented by Chemical Formula 1 including: 1) refluxing a mixture of 6-bromo-N-methyl-2-naphthylamine, Proton-sponge and tert-butyl bromoacetate to prepare Compound B represented by Chemical Formula 2; 2) stirring a mixture of Compound B, benzoxazole, Pd(II) OAc, $PPh_3$, CuI and $CsCO_3$ to prepare Compound A represented by Chemical Formula 3; and 3) mixing Compound A with 1-hydroxybenzotriazole and Compound D represented by Chemical Formula 4 and reacting the mixture:

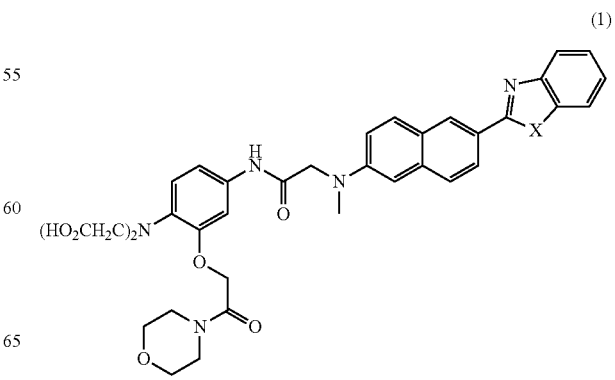

(1)

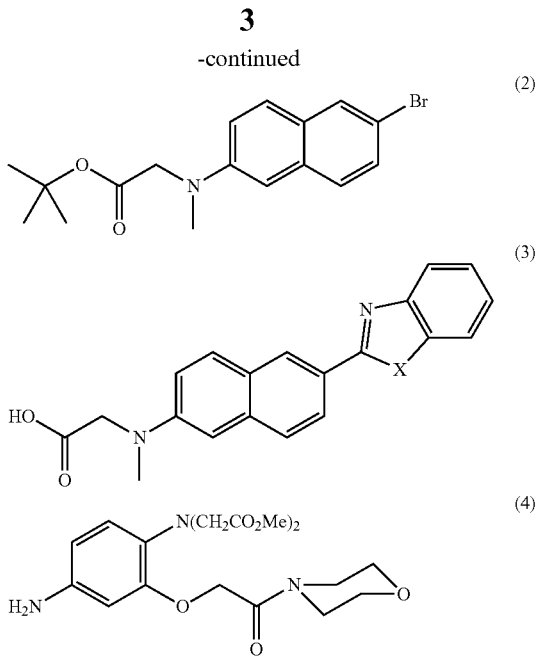

wherein X is O, S or NH.

In another general aspect, the present disclosure provides a method for selectively imaging the distribution of calcium ions in a living cell or tissue using the two-photon fluorescent probe represented by Chemical Formula 1.

In another general aspect, the present disclosure provides a method for imaging $Na^+/Ca^{2+}$ exchange in a living cell or tissue using the two-photon fluorescent probe represented by Chemical Formula 1 and a two-photon fluorescent probe for detecting sodium ions.

Other features and aspects will be apparent from the following detailed description, the drawings, and the claims.

BRIEF DESCRIPTION OF THE DRAWINGS

The above and other objects, features and advantages of the present disclosure will become apparent from the following description of certain exemplary embodiments given in conjunction with the accompanying drawings, in which.

Figure 1:
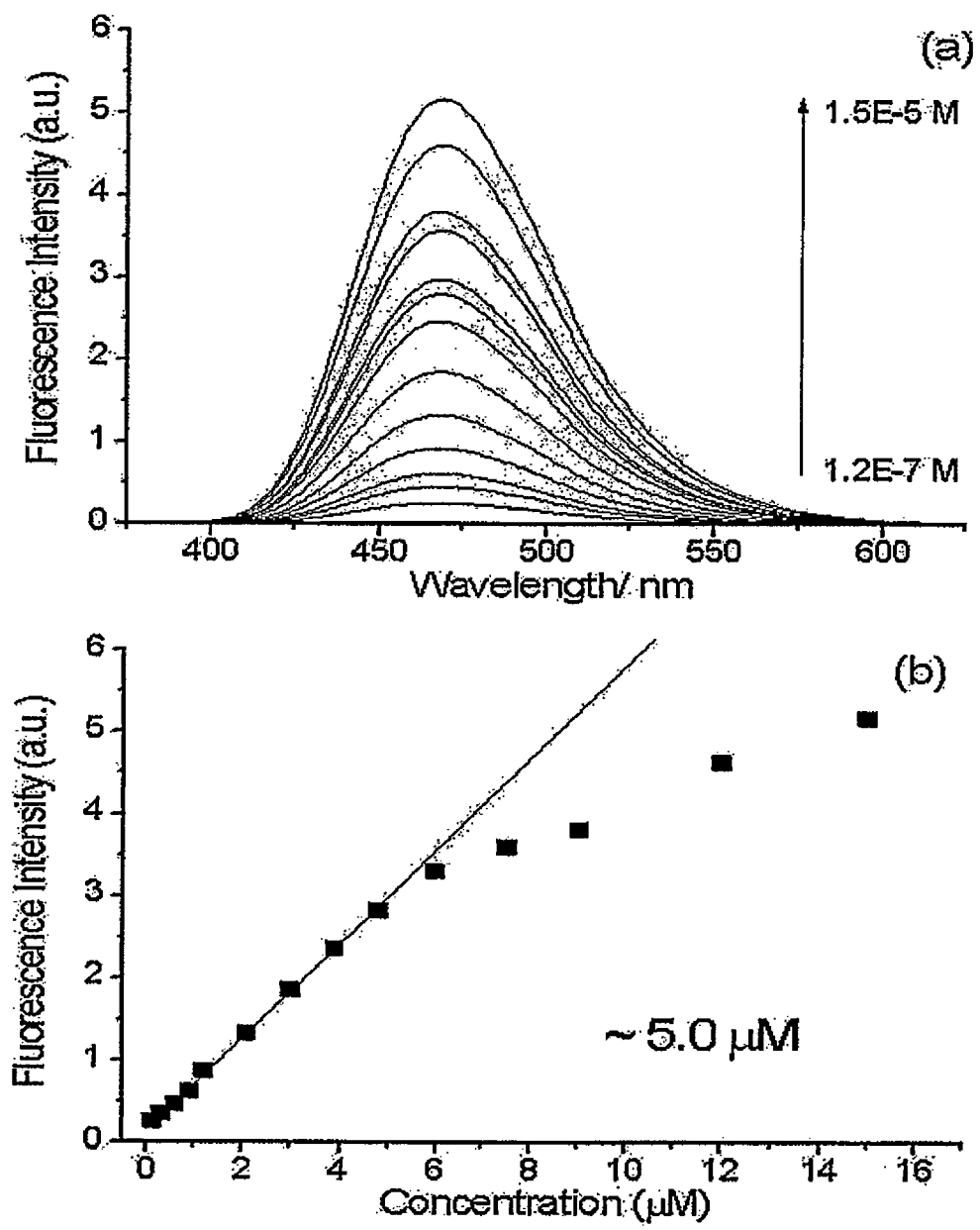
FIG. 1 shows one-photon fluorescence spectra of BCa1 and fluorescence intensity of BCa1 depending on concentration in $H_2O$.

It should be understood that the appended drawings are not necessarily to scale, presenting a somewhat simplified representation of various preferred features illustrative of the basic principles of the disclosure. The specific design features of the disclosure as disclosed herein, including, for example, specific dimensions, orientations, locations and shapes, will be determined in part by the particular intended application and use environment.

DETAILED DESCRIPTION OF EMBODIMENTS

The advantages, features and aspects of the present disclosure will become apparent from the following description of the embodiments with reference to the accompanying drawings, which is set forth hereinafter. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. The terminology used herein is for the purpose of describing particular embodiments only and is not intended to be limiting of the example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail.

The present disclosure provides a two-photon fluorescent probe represented by Chemical Formula 1:

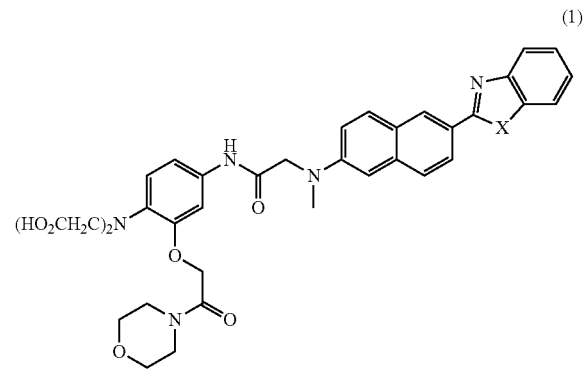

In Chemical Formula 1, X may be O, S or NH, specifically O.

The two-photon fluorescent probe represented by Chemical Formula 1 according to the present disclosure may be used to detect calcium ions in a living cell or tissue.

The two-photon fluorescent probe represented by Chemical Formula 1 comprises 2-(2'-morpholino-2'-oxoethoxy)-N,N-bis(hydroxycarbonylmethyl)aniline (MOBHA) as a calcium cation receptor and 6-(benzo[d]oxazol-2'-yl)-2-(N,N-dimethylamino)naphthalene as a reporter.

Further, the present disclosure provides a method for preparing the two-photon fluorescent probe represented by Chemical Formula 1 comprising: 1) refluxing a mixture of 6-bromo-N-methyl-2-naphthylamine, Proton-sponge and tert-butyl bromoacetate to prepare Compound B represented by Chemical Formula 2; 2) stirring a mixture of Compound B, benzoxazole, Pd(II) OAc, PPh$_3$, CuI and CsCO$_3$ to prepare Compound A represented by Chemical Formula 3; and 3) mixing Compound A with 1-hydroxybenzotriazole and Compound D represented by Chemical Formula 4 and reacting the mixture:

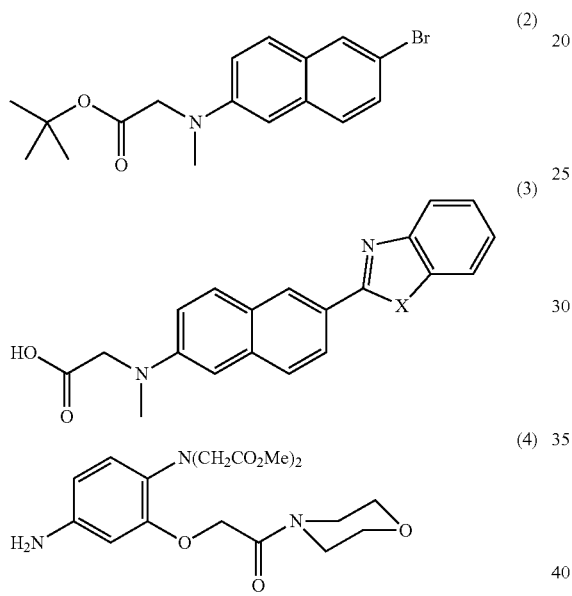

In Chemical Formula 3, X may be O, S or NH, specifically O,

Specifically examples of the method for preparing the two-photon fluorescent probe represented by Chemical Formula 1 according to the present disclosure are given in the Examples section.

The present disclosure further provides a method for selectively imaging the distribution of calcium ions in a living cell or tissue using the two-photon fluorescent probe represented by Chemical Formula 1. More specifically, the distribution of calcium ions near the cell membrane may be selectively imaged.

The two-photon fluorescent probe represented by Chemical Formula 1 according to the present disclosure reacts with calcium cations to exhibit strong two-photon fluorescence and may be selectively and easily loaded into the cell membrane by forming a complex with a calcium ion. Further, it allows imaging of the distribution of calcium cations in a living cell or tissue since it can selectively detect calcium ions in the living cell or tissue at a depth of 100 to 200 μm for more than 60 minutes.

The present disclosure further provides a method for imaging Na$^+$/Ca$^{2+}$ exchange in a living cell or tissue using the two-photon fluorescent probe represented by Chemical Formula 1 and a two-photon fluorescent probe for detecting sodium ions.

The two-photon fluorescent probe for detecting sodium ions may be ANa1 represented by the following formula, but is not limited thereto:

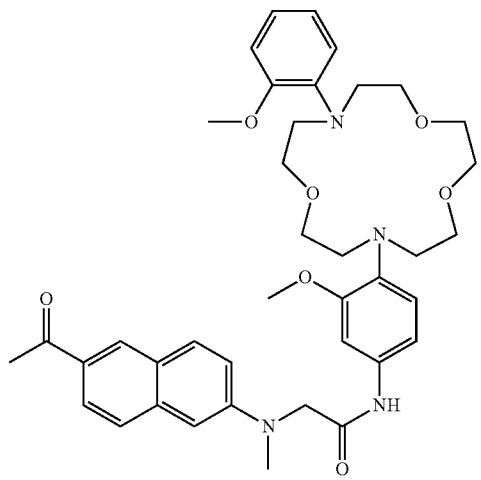 [SMILES: COc1ccccc1N1CCOCCOCCN(c2ccc(NC(=O)CN(C)c3ccc4cc(C(C)=O)ccc4c3)cc2OC)CCOCC1]

By staining a living cell or tissue with the two probes of different fluorescent colors, the calcium and sodium activities can be imaged simultaneously at different channels.

EXAMPLES

The examples and experiments will now be described. The following examples and experiments are for illustrative purposes only and not intended to limit the scope of this disclosure.

Example 1

Preparation of Two-Photon Fluorescent Probe (BCa1)

6-Bromo-N-methyl-2-naphthylamine and 2-(2'-morpholino-2'-oxoethoxy)-4-nitro-N,N-bis(hydroxycarbonylmethyl) aniline (Compound C) were synthesized according to known methods. Other compounds were synthesized as follows.

[Scheme 1]

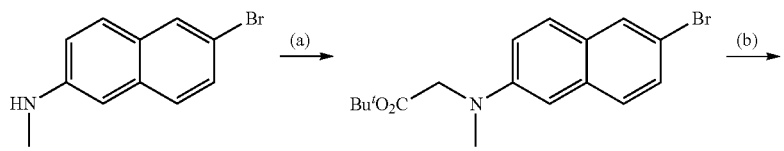

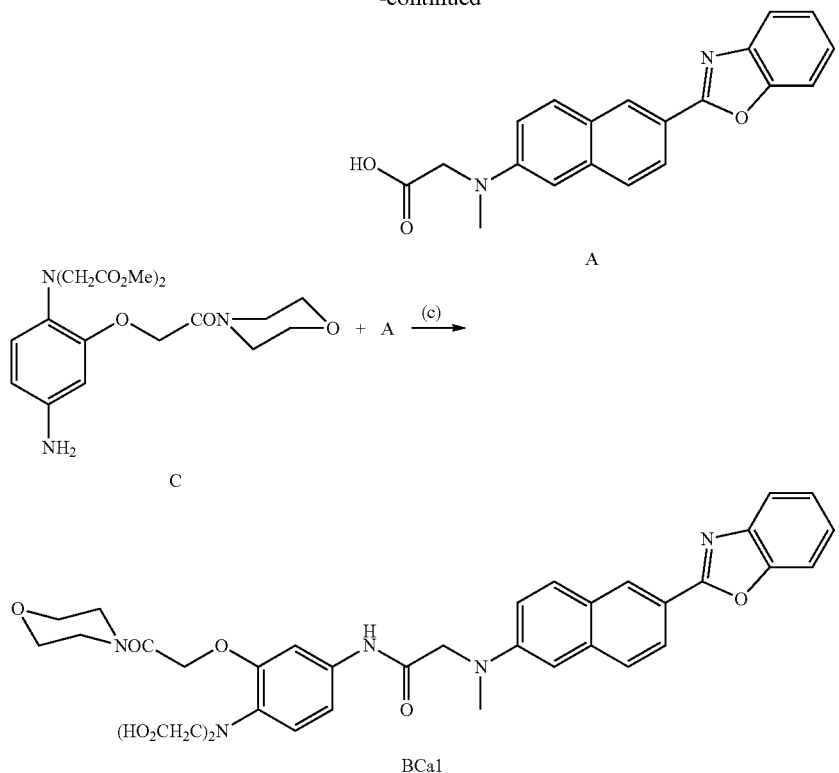

The reaction conditions in Scheme 1 are: (a)=t-butyl bromoacetate/Proton-sponge/MeCN, (b)=benzoxazole/Pd(II)OAc/PPh$_3$/CuI/CsCO$_3$/DMF and CF$_3$CO$_2$H/CH$_2$Cl$_2$, (c)= DCC/HOBt/CH$_2$Cl$_2$ and KOH/EtOH/dioxane.

1) Preparation of 2-bromo-6-N-(tert-butoxycarbonyl) methyl-N-methylaminonaphthalene (Compound B)

A mixture of 6-bromo-N-methyl-2-naphthylamine (2.0 g, 8.5 mmol), Proton-sponge (2.0 g, 9.4 mmol) and tert-butyl bromoacetate (2.0 g, 1.5 mL, 10.2 mmol) was refluxed in MeCN under N$_2$ for 12 hours. The resulting product was extracted with ethyl acetate, washed with brine, dried with MgSO$_4$, concentrated, and then purified by silica gel column chromatography using hexane/ethyl acetate (5:1) as eluent.

Yield: 2.6 g (87%);
mp: 63° C.;
IR (KBr): 1,736 cm$^{-1}$;
$^1$H NMR (400 MHz, CDCl$_3$): δ 7.79 (d, 1H, J=2 Hz), 7.57 (d, 1H, J=9 Hz), 7.48 (d, 1H, J=9 Hz), 7.38 (dd, 1H, J=9, J=2 Hz), 7.05 (dd, 1H, J=9, J=2 Hz), 6.82 (d, 1H, J=2 Hz), 4.04 (s, 2H), 3.14 (s, 3H), 1.40 (s, 9H);
$^{13}$C NMR (100 MHz, CDCl$_3$): δ=170.3, 147.5, 133.8, 129.8, 129.7, 128.4, 128.3, 128.2, 116.7, 115.7, 106.7, 82.2, 56.0, 40.5, 28.7 ppm.
Anal. Calcd. for C$_{17}$H$_{20}$BrNO$_2$: C, 58.30; H, 5.76; N, 4.00. Found: C, 58.43; H, 5.65; N, 4.06.

2) Preparation of Compound A

A mixture of Compound B (1.0 g, 2.9 mmol), benzoxazole (0.41 g, 3.4 mmol), Pd(II)OAc (0.033 g, 0.15 mmol), PPh$_3$ (0.073 g, 0.29 mmol), CuI (0.11 g, 0.58 mmol) and CsCO$_3$ (1.1 g, 3.5 mmol) was stirred in DMF under N$_2$ at 140° C. for 12 hours. The reaction mixture was filtered, diluted with ethyl acetate, washed with brine, dried with MgSO$_4$, and concentrated. The resulting crude product was purified by silica gel column chromatography using hexane/ethyl acetate (3:1) as eluent.

Yield: 0.64 g (57%);
mp: 165° C.;
IR (KBr): 1,738 cm$^{-1}$;
$^1$H NMR (400 MHz, CDCl$_3$): δ 8.56 (d, 1H, J=2 Hz), 8.14 (dd, 1H, J=9, J=2 Hz), 7.78 (d, 1H, J=9 Hz), 7.73 (m, 1H), 7.69 (d, 1H, J=9 Hz), 7.54 (m, 1H), 7.30 (m, 2H), 7.06 (dd, 1H, J=9, J=2 Hz), 6.85 (d, 1H, J=2 Hz), 4.05 (s, 2H), 3.15 (s, 3H), 1.41 (s, 9H);
$^{13}$C NMR (100 MHz, CDCl$_3$): δ=169.7, 164.0, 150.9, 148.6, 142.6, 136.8, 130.3, 128.1, 127.0, 126.4, 124.7, 124.5, 124.4, 120.7, 119.9, 116.2, 110.6, 106.4, 82.1, 55.7, 40.2, 28.4 ppm.
Anal. Calcd. for C$_{24}$H$_{24}$N$_2$O$_3$: C, 74.21; H, 6.23; N, 7.21. Found: C, 74.33; H, 6.35; N, 7.11.

After adding CF$_3$CO$_2$H (2 mL) to a solution of the ester (0.50 g, 1.3 mmol) in CH$_2$Cl$_2$ (10 mL), the mixture was stirred under N$_2$ for 24 hours. The solvent was removed under vacuum and the resulting product was washed with hexane and then filtered.

Yield: 0.29 g (68%);
mp: 188° C.;
IR (KBr): 2,900, 1,718 cm$^{-1}$;
$^1$H NMR (400 MHz, CDCl$_3$/CD$_3$OD): δ 8.57 (d, 1H, J=2 Hz), 8.12 (dd, 1H, J=9, J=2 Hz), 7.84 (d, 1H, J=9 Hz), 7.75 (d, 1H, J=9 Hz), 7.71 (m, 1H), 7.60 (m, 1H), 7.36 (m, 2H), 7.16 (dd, 1H, J=9, J=2 Hz), 6.94 (d, 1H, J=2 Hz), 4.22 (s, 2H), 3.22 (s, 3H);
$^{13}$C NMR (100 MHz, CDCl$_3$/CD$_3$OD): δ=173.1, 164.3, 150.9, 148.8, 142.1, 137.0, 130.6, 128.4, 127.3, 126.4, 125.2, 124.9, 124.6, 120.3, 119.6, 116.4, 110.8, 106.3, 54.6, 40.1 ppm.

Anal. Calcd. for $C_{20}H_{16}N_2O_3$: C, 72.28; H, 4.85; N, 8.43. Found: C, 72.17; H, 4.91; N, 8.40.

3) Preparation of 2-(2'-morpholino-2'-oxoethoxy)-N,N-bis(methoxycarbonylmethyl)-1,4-phenylenediamine (Compound D)

Compound C (0.67 g, 1.6 mmol) and Pd/C (0.033 g, 0.31 mmol) were mixed with ethyl acetate (50 mL) and shaken under hydrogen for 12 hours. The reaction mixture was filtered with Celite and the solvent was removed under vacuum.

Yield: 0.58 g (92%);
IR (KBr): 1,740, 1,642 cm$^{-1}$;
$^1$H NMR (400 MHz, CDCl$_3$): δ 6.77 (d, 1H, J=8 Hz), 6.26 (d, 1H, J=2 Hz), 6.17 (dd, 1H, J=8, J=2 Hz), 4.65 (s, 2H), 3.97 (s, 4H), 3.59 (s, 6H), 3.58-3.53 (m, 8H);
$^{13}$C NMR (100 MHz, CDCl$_3$): δ=171.6, 166.6, 151.6, 143.3, 130.6, 122.6, 108.6, 103.0, 68.4, 66.8, 54.0, 51.6, 45.8 ppm.
Anal. Calcd. for $C_{18}H_{25}N_3O_7$: C, 54.68; H, 6.37; N, 10.63. Found: C, 54.59; H, 6.50; N, 10.58.

4) Preparation of Two-Photon Fluorescent Probe (Bca1)

A mixture of Compound A (0.10 g, 0.30 mmol), 1,3-dicyclohexyl carbodiimide (0.060 g, 0.30 mmol) and 1-hydroxybenzotriazole (0.034 g, 0.25 mmol) was stirred in CH$_2$Cl$_2$ for 1 hour. After adding Compound D (0.10 g, 0.25 mmol) dissolved in CH$_2$Cl$_2$, the mixture was stirred under N$_2$ for 12 hours. The resulting mixture was stirred, and the filtrate was concentrated under vacuum. The resulting crude product was purified by silica gel column chromatography using CHCl$_3$/MeOH (20:1) as eluent.

Yield: 0.12 g (66%);
mp: 80° C.;
IR (KBr): 1,743, 1,626, 1,516 cm$^{-1}$;
$^1$H NMR (400 MHz, CDCl$_3$): δ 8.65 (d, 1H, J=2 Hz), 8.27 (s, 1H), 8.23 (dd, 1H, J=9, J=2 Hz), 7.88 (d, 1H, J=9 Hz), 7.79 (d, 1H, J=9 Hz), 7.76 (m, 1H), 7.59 (m, 1H), 7.38 (d, 1H, J=2 Hz), 7.34 (m, 2H), 7.16 (dd, 1H, J=9, J=2 Hz), 7.09 (d, 1H, J=2 Hz), 6.87 (m, 2H), 4.74 (s, 2H), 4.13 (s, 4H), 4.10 (s, 2H), 3.66 (s, 6H), 3.50-3.61 (m, 8H), 3.22 (s, 3H);
$^{13}$C NMR (100 MHz, CDCl$_3$): δ=171.6, 168.2, 166.2, 163.6, 150.7, 150.1, 148.6, 142.3, 136.2, 135.9, 133.0, 130.6, 127.9, 127.3, 126.9, 125.0, 124.9, 124.7, 121.3, 120.6, 119.8, 116.6, 113.8, 110.7, 107.5, 107.3, 67.5, 66.8, 60.7, 53.8, 52.1, 45.7, 40.4 ppm.
Anal. Calcd. for $C_{38}H_{39}N_5O_9$: C, 64.31; H, 5.54; N, 9.87. Found: C, 64.71; H, 5.60; N, 9.79.

After gradually adding KOH (1M, 0.35 mL, 0.35 mmol) to a solution of the intermediate (0.10 g, 0.14 mmol) in MeOH/dioxane (1/1 mL), the reaction mixture was stirred for 15 hours. After evaporating the solvent, the resulting mixture was dissolved in distilled water (20 mL), extracted with ether, and the aqueous solution was collected. After slowly adding HCl (1 M, 0.35 mL, 0.35 mmol), two drops of AcOH were added. The resulting precipitate was collected and washed with distilled water.

Yield: 57 mg (60%);
mp: 162° C.;
IR (KBr): 2,970, 1,626, 1,514 cm$^{-1}$;
$^1$H NMR (400 MHz, CDCl$_3$/CD$_3$OD): δ 8.60 (d, 1H, J=2 Hz), 8.16 (dd, 1H, J=9, J=2 Hz), 7.88 (d, 1H, J=9 Hz), 7.78 (d, 1H, J=9 Hz), 7.73 (m, 1H), 7.60 (m, 1H), 7.37 (d, 1H, J=2 Hz), 7.34 (m, 2H), 7.17 (dd, 1H, J=9, J=2 Hz), 7.04 (d, 1H, J=2 Hz), 6.93 (m, 2H), 4.76 (s, 2H), 4.14 (s, 2H), 4.03 (s, 4H), 3.51-3.59 (m, 8H), 3.24 (s, 3H);
$^{13}$C NMR (100 MHz, CDCl$_3$): δ=172.9, 168.2, 166.4, 163.6, 150.7, 149.9, 149.7, 142.4, 136.9, 135.2, 133.7, 130.6, 128.2, 127.4, 125.9, 125.6, 125.3, 124.5, 120.0, 119.8, 119.6, 117.1, 112.8, 111.3, 106.7, 106.2, 105.8, 67.0, 66.7, 56.1, 54.1, 45.6 ppm.
Anal. Calcd. for $C_{36}H_{35}N_5O_9$: C, 63.43; H, 5.18; N, 10.27. Found: C, 63.22; H, 5.21; N, 10.19.

Test Example

1) Water solubility

A stock solution (1.0×10$^{-2}$M) was prepared by dissolving the dye (BCa1) in DMSO. The solution was diluted (to 6.0×10$^{-3}$ to 6.0×10$^{-5}$ M) and transferred to a cuvette holding H$_2$O (3.0 mL) using a microsyringe. In all cases, the concentration of DMSO in H$_2$O was maintained at 0.20. Fluorescence intensity plotted against the dye concentration showed linearity at low concentrations and was bent downward at high concentrations (see FIG. 1). The highest concentration in the linear region was determined as the solubility of BCa1, which was about 5.0 μM in water, being sufficient to stain cells.

One-photon fluorescence spectra of BCa1 are shown in FIG. 1 (a), and the fluorescence intensity of BCa1 in H$_2$O depending on concentrations is shown in FIG. 1 (b). Excitation wavelength was 360 nm.

2) Spectroscopic Measurements

Absorption spectra were measured using a Hewlett-Packard 8453 diode array spectrophotometer, and fluorescence spectra were measured using an Amico-Bowman series 2 emission spectrometer having 1 cm standard quartz cell. Fluorescence quantum yield was determined using coumarin 307 (Φ=0.95 in MeOH) according to a previously known method.

Figure 2:
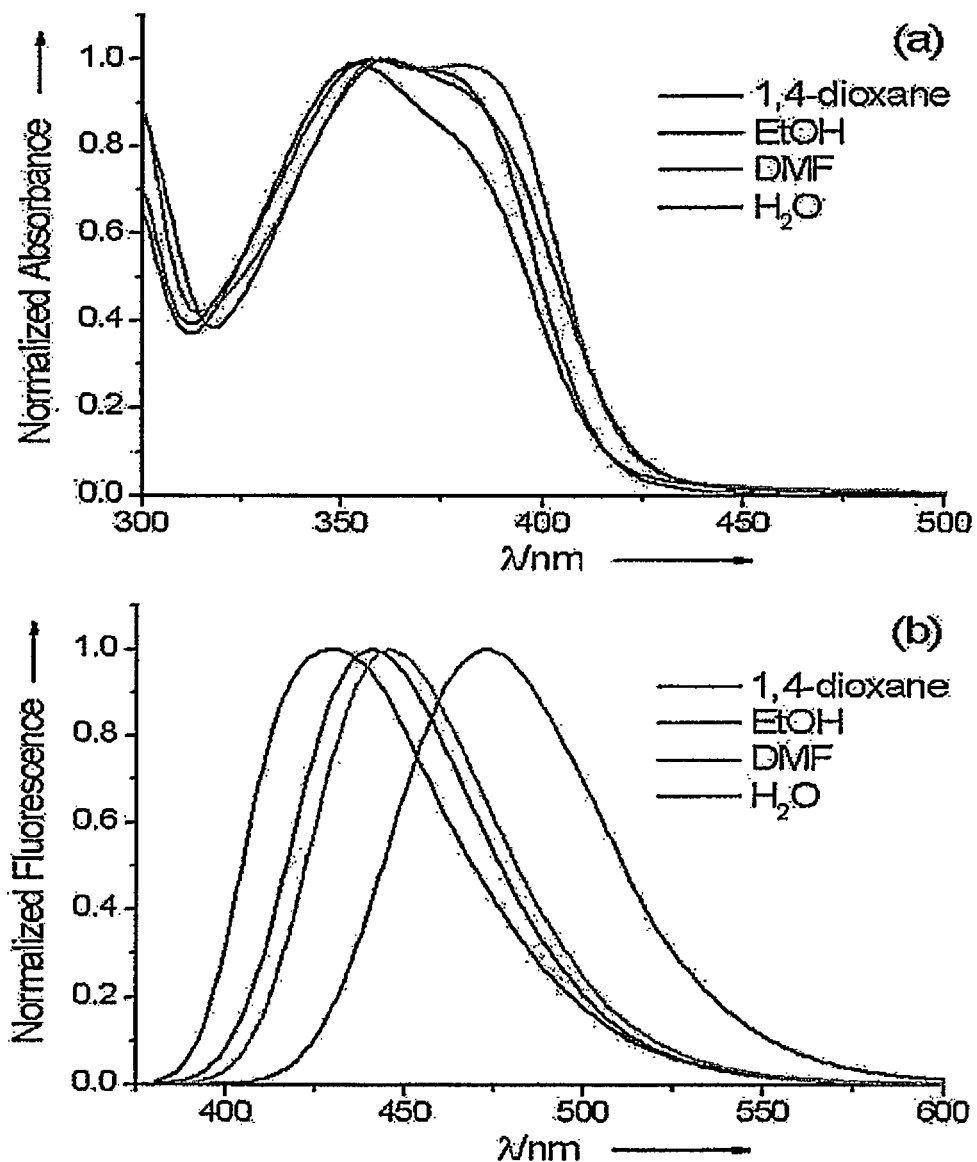
FIG. 2 shows normalized absorption and emission spectra of BCa1 in 1,4-dioxane, EtOH, DMF and $H_2O$.

Normalized absorption spectra of BCa1 in 1,4-dioxane, EtOH, DMF and H$_2$O are shown in FIG. 2 (a), and normalized emission spectra of BCa1 in 1,4-dioxane, EtOH, DMF and H$_2$O are shown in FIG. 2 (b).

As seen from FIG. 2, the absorption and emission spectra of BCa1 showed gradual red shift with the increase of the solvent polarity.

Figure 3:
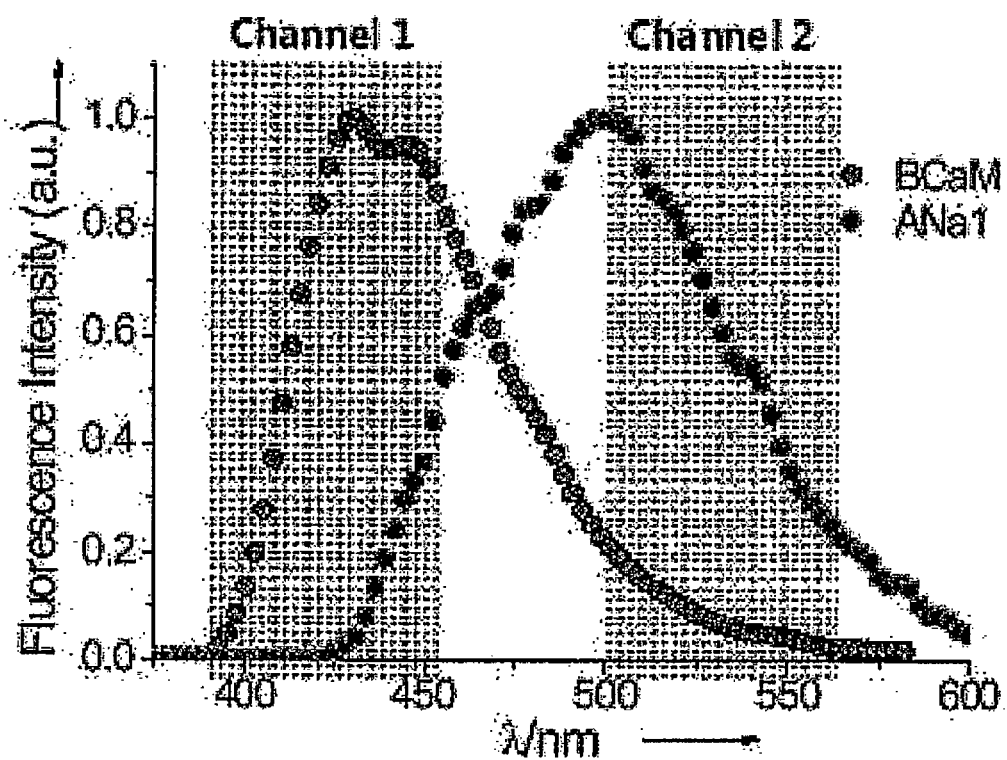
FIG. 3 shows normalized emission spectra of BCa1 and ANa1 in HeLa cells.

FIG. 3 shows the normalized emission spectra of BCa1 and ANa1 in HeLa cells. As seen from FIG. 3, the emission band of BCa1 is distinguished well from the emission band of ANa1.

Figure 4:
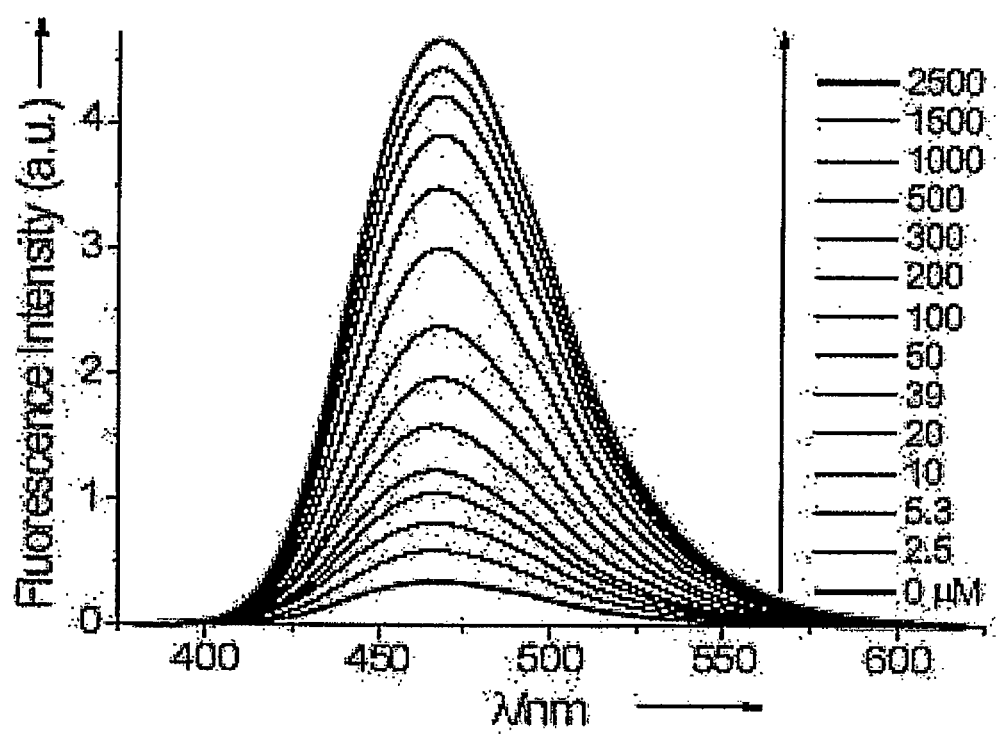
FIG. 4 shows one-photon fluorescence spectra of BCa1.

FIG. 4 shows one-photon fluorescence spectra of 1 μM BCa1 (30 mM 3-(N-morpholino)propanesulfonic acid (MOPS), 100 mM KCl, pH 7.2) in the presence of free Ca$^{2+}$ (0 to 2.5 mM). As seen from FIG. 4, when Ca$^{2+}$ was added to BCa1 in the MOPS buffer (30 mM, 100 mM KCl, pH 7.2), the fluorescence intensity increased abruptly with the metal ion concentration. This is caused by the blocking of photo-induced electron transfer (PET) resulting from complexation with the metal ions. Almost similar result was observed for the two-photon process.

Photophysical test results for ANa1 and BCa1 are shown in Table 1.

TABLE 1

| | $\lambda^{(1)}_{max}/\lambda^{fl}_{max}$ | Φ | $K^{TP}_d/K^i_d$ | FEF | $\lambda^{(2)}_{max}$ | δΦ |
|---|---|---|---|---|---|---|
| BCa1 | 360/470 | 0.07 | — | — | nd | nd |
| BCa1 + Ca$^{2+}$ | 360/470 | 0.98 | 89/78 μM | 13(14) | 780 | 150 |

TABLE 1-continued

| | $\lambda^{(1)}_{max}/\lambda^{fl}_{max}$ | $\Phi$ | $K^{TP}_d/K^i_d$ | FEF | $\lambda^{(2)}_{max}$ | $\delta\Phi$ |
|---|---|---|---|---|---|---|
| ANa1 | 367/500 | 0.08 | — | — | nd | nd |
| ANa1 + Na$^+$ | 367/500 | 0.65 | 20/26 mM | 8(8) | 780 | 95 |

$\lambda^{(1)}_{max}$: One-photon absorption and emission wavelength (nm)
$\Phi$: Fluorescence photon efficiency (error range: ±10%)
$K^{TP}_d$: Dissociation constant for Ca$^{2+}$ measured in two-photon process in buffer
$K^i_d$: Dissociation constant for Ca$^{2+}$ measured in two-photon process in cells
FEF: Fluorescence enhancement factor ((F − F$_{min}$)/F$_{min}$ = FEF), Values in parentheses are for two-photon process
$\lambda^{(2)}_{max}$: Two-photon excitation wavelength (nm)
$\delta\Phi$: Two-photon operational cross section at $10^{-50}$ cm$^4$ s/photon (GM) (error range: ±15%)
nd: Not determinable because of too weak two-photon fluorescence intensity
$\lambda^{fl}_{max}$: Value measured in large unilamellar vesicles (LUVs) composed of 1,2-dipalmitoyl-sn-glycero-3-phosphocholine/cholesterol (DPPC/CHL), raft mixture and 1,2-dioleoylsn-glycero-3-phosphocholine (DOPC)
$K^{OP}_d$ values measured in the buffer and LUVs were 90 ± 2 μM and 81 ± 4 μM, respectively.

Figure 5:
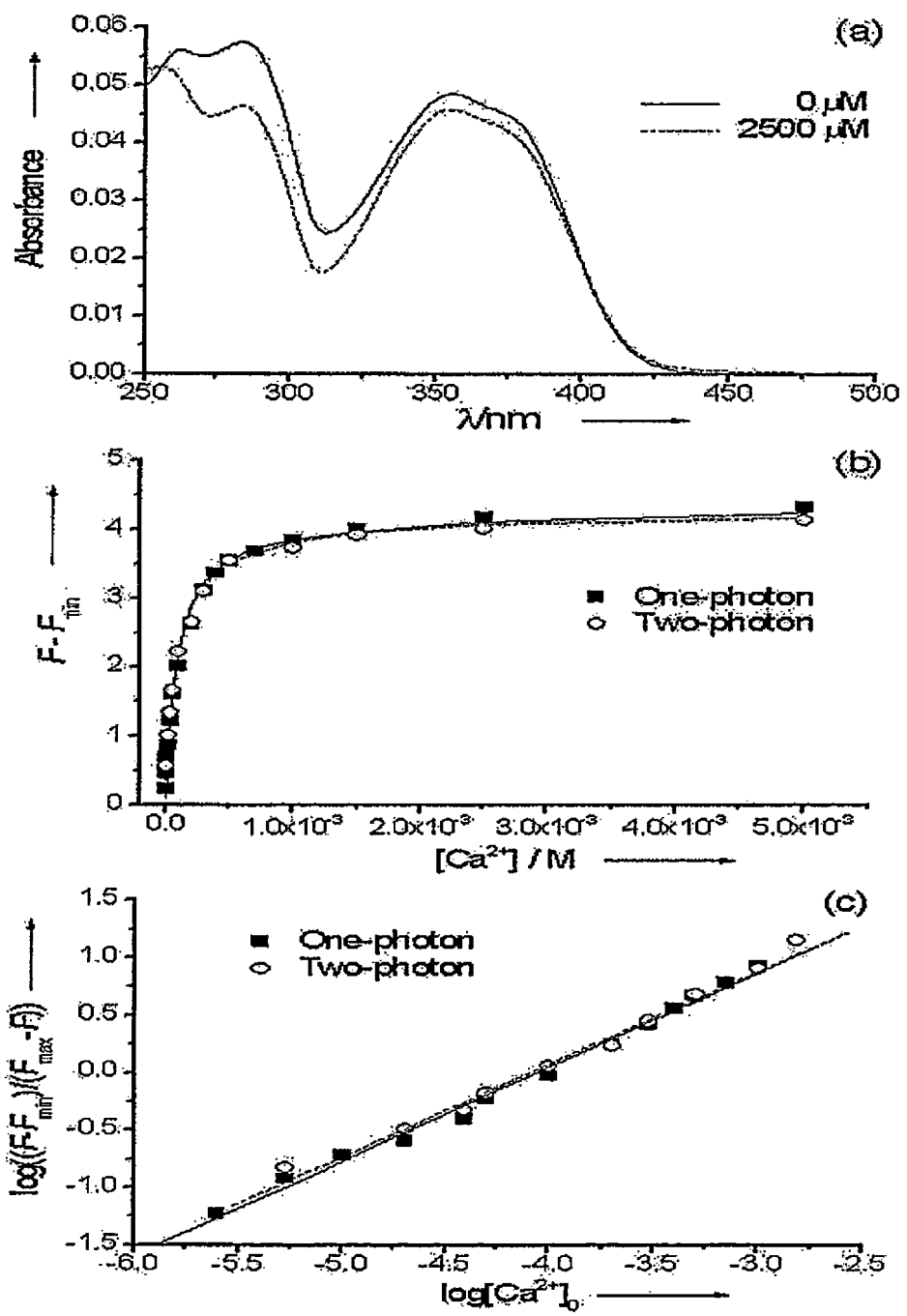
FIG. 5 shows one-photon absorption curves of BCa1, one-photon and two-photon fluorescence titration curves of BCa1, and one-photon and two-photon Hill curves of BCa1.

One-photon absorption curves of 1 μM BCa1 (30 mM MOPS, 100 mM KCl, pH 7.2) complex in the presence of free Ca$^{2+}$ are shown in FIG. 5 (*a*), one-photon and two-photon fluorescence titration curves are shown in FIG. 5 (*b*), and one-photon and two-photon Hill curves are shown in FIG. 5 (*c*).

The dissociation constants of BCa1 for the one-photon and two-photon processes ($K^{OP}_d$ and $K^{TP}_d$) were calculated from the fluorescence titration curves of FIG. 5 (*b*).

Figure 6:
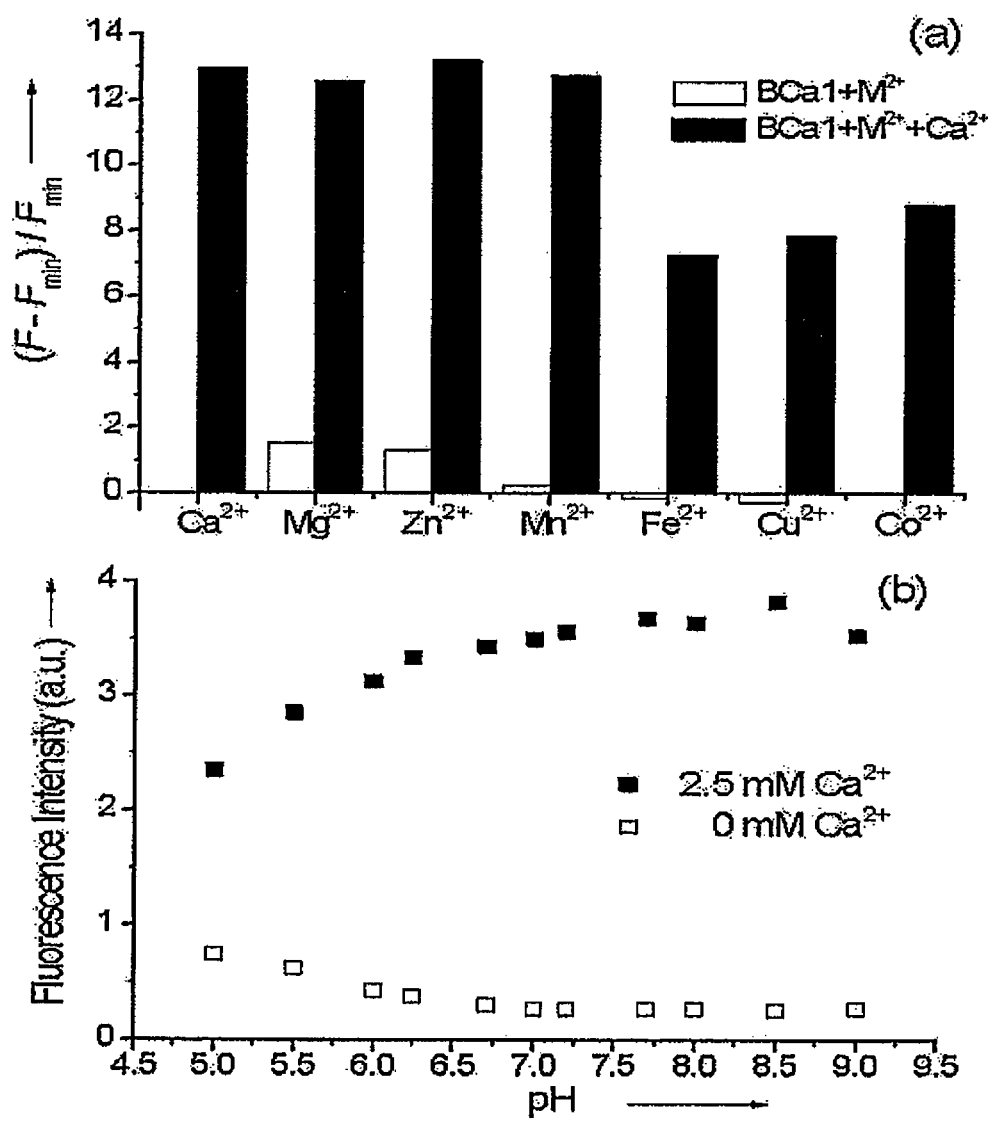
FIG. 6 shows relative fluorescence intensity of BCa1 for various cations and effect of pH on one-photon fluorescence intensity of BCa1.

Relative fluorescence intensity of 1 μM BCa1 for various cations are shown in FIG. 6 (*a*), and the effect of pH on one-photon fluorescence intensity of BCa1 is shown in FIG. 6 (*b*). BCa1 exhibited weak responses to Mg$^{2+}$, Zn$^{2+}$ and Mn$^{2+}$, and no response at all to Fe$^{2+}$, Cu$^{2+}$ and Co$^{2+}$. Thus, the probe allows selective detection of Ca$^{2+}$ without minimized interference from other biologically relevant cations. Further, BCa1 was not affected by pH.

Figure 7:
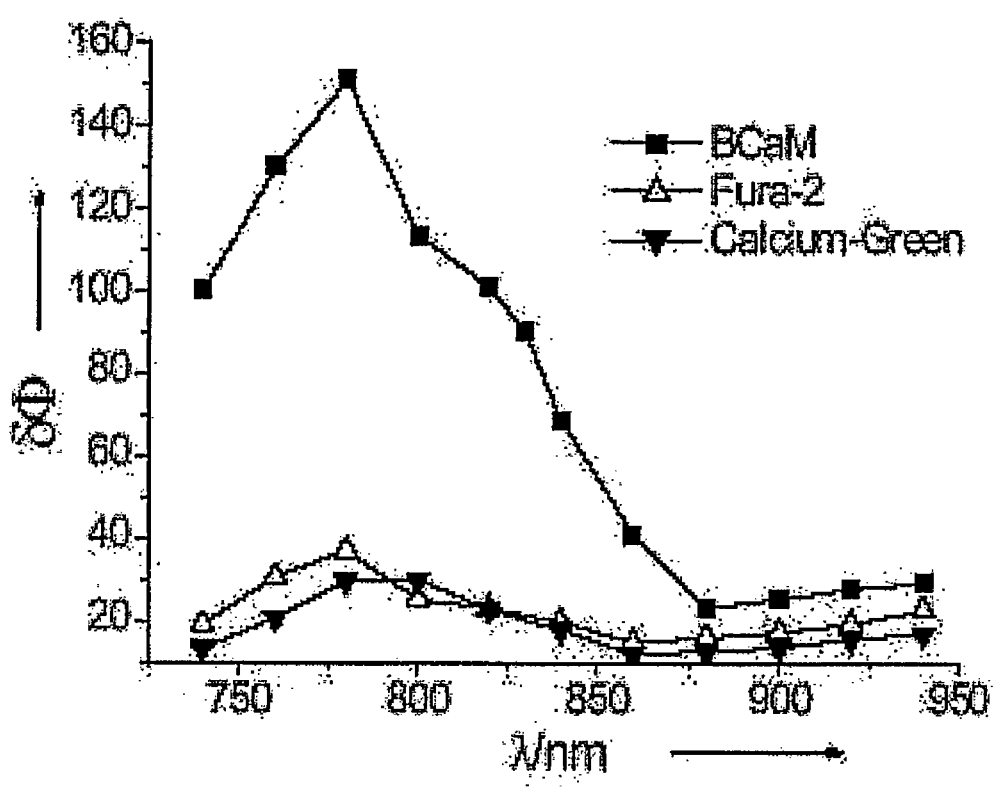
FIG. 7 shows two-photon fluorescence operational spectra.

Two-photon operational emission δΦ of BCa1 in the MOPS buffer containing excess Ca$^{2+}$ was 150 GM at 780 nm, 3- to 5-fold improved over Calcium-Green-Ca$^{2+}$ or Fura-2-Ca$^{2+}$ (see FIG. 7). Thus, it can be seen that staining of cells with BCa1 can provide brighter TPM images as compared to other commercially available probes.

3) Preparation of LUVs

LUVs for the measurement of one-photon and two-photon spectra were prepared from a hydrated suspension of multi-lamellar vesicles by means of extrusion. Lipids were dissolved in CHCl$_3$/MeOH (95/5 vol %) and then dried under N$_2$ flow in vacuum. The resulting film was hydrated in MOPS buffer (30 mM MOPS, 100 mM KCl, pH 7.2) by shaking at 60° C. until the suspension became homogeneous. The mixture was subjected to 3 freeze-thaw cycles, and LUVs were extruded therefrom by passing through a membrane having 100 nm pores (Avanti Polar Lipids). To stain the vesicles, BCa1 dissolved in DMSO was added and then 30 minutes was allowed to pass. The proportion of the vesicles to the probe was 300:1. Temperature was measured using a digital thermometer having a precision of 0.1° C.

Figure 8:
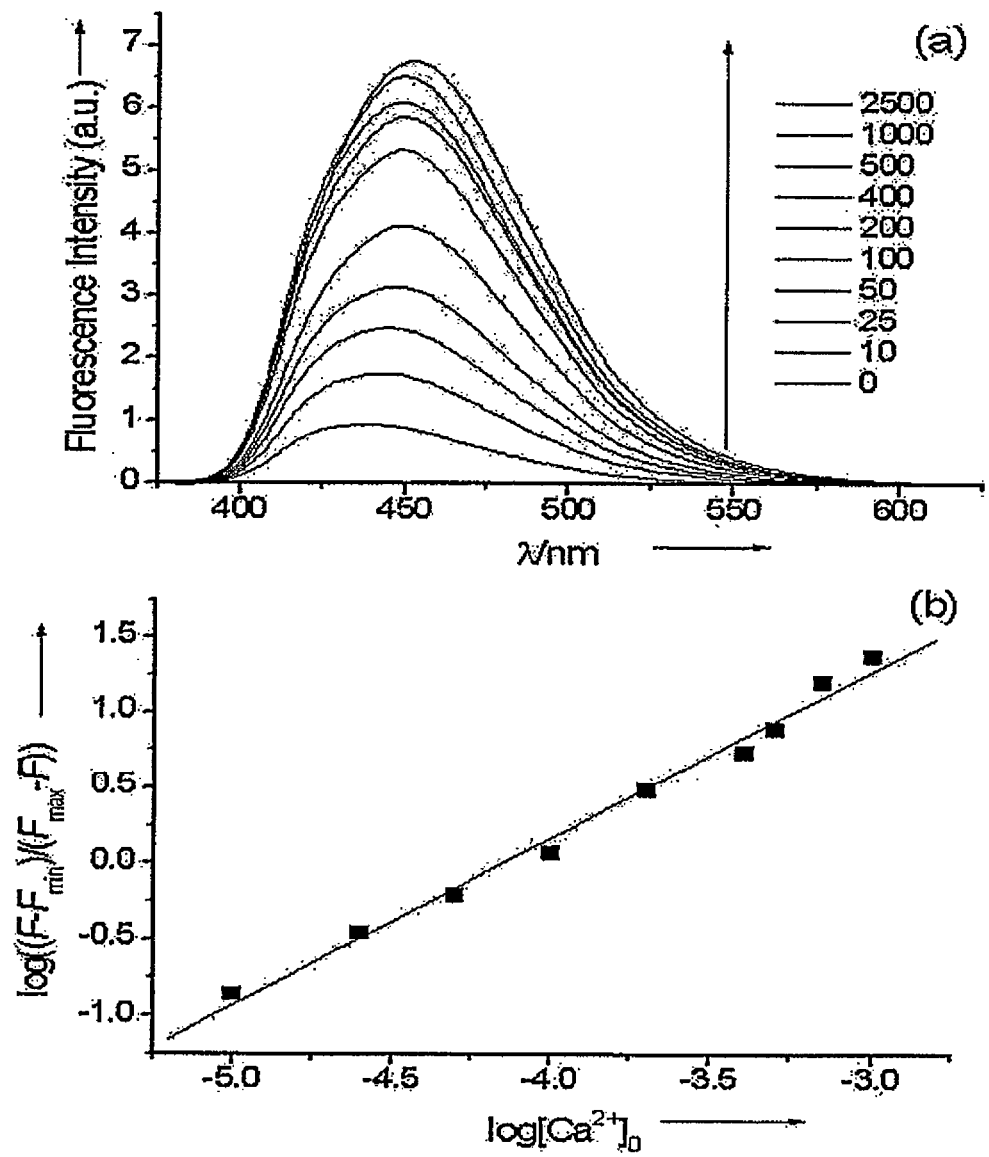
FIG. 8 shows one-photon fluorescence spectra of BCa1 and a Hill curve of BCa1.

One-photon fluorescence spectra of complexes of free Ca$^{2+}$ (0 to 2.5 mM) and 1 μM BCa1 for LUVs composed of DOPC/sphingomyelin/cholesterol (1:1:1, raft mixture) are shown in FIG. 8 (*a*), and Hill curves are shown in FIG. 8 (*b*).

Figure 9:
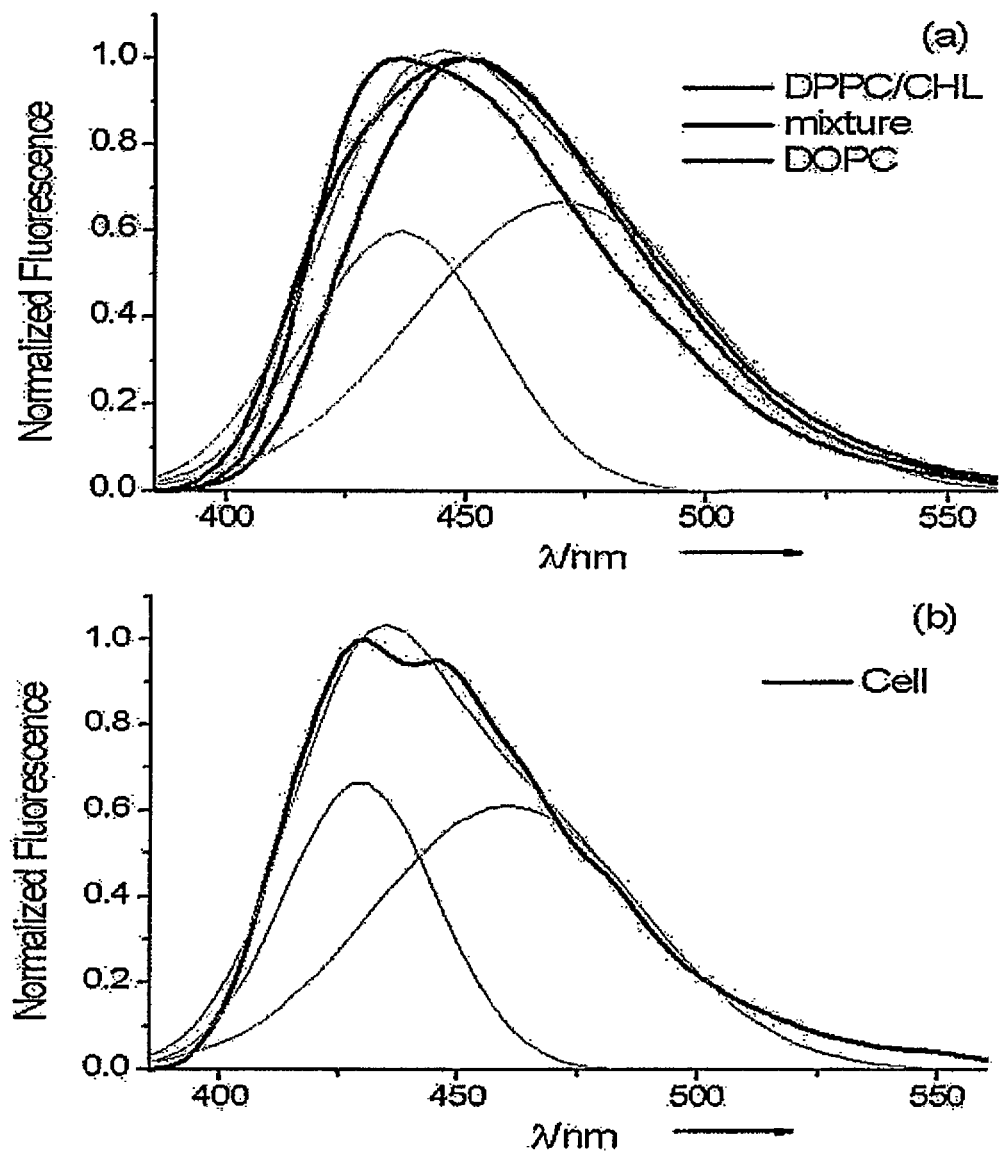
FIG. 9 shows normalized emission spectra of BCa1 in LUVs and normalized emission spectra of BCa1 in HeLa cells.

Normalized emission spectra of BCa1 containing free Ca$^{2+}$ (2.5 mM) in LUVs composed of DPPC/CHL (black curve), DOPC/sphingomyelin/CHL (1:1:1, raft mixture, blue curve) and DOPC (pink curve) at 25±0.5° C. are shown in FIG. 9 (*a*), and normalized emission spectra of BCa1 in HeLa cells are shown in FIG. 9 (*b*). The spectra for the raft mixture matched well with the two (azure) Gaussian curves having maximum emissions at 436 and 467 nm. And, the spectra obtained from the cells matched well with the two (green) Gaussian curves having maximum emissions at 430 and 460 nm.

4) Measurement of Two-Photon Absorption (TPA) Cross Section

TPA cross section (6) was measured by femtosecond (fs) fluorescence spectroscopy. BCa1 was dissolved in 30 mM MOPS buffer (2.5 mM CaCl$_2$, 100 mM KCl, pH 7.2) to a concentration of 5.0×10$^{-6}$ M, and two-photon excited fluorescence (TPEF) was measured at 740 to 940 nm using fluorescein (8.0×10$^{-6}$M, pH=11). TPEF intensity of reference and sample was determined at the same excitation wavelength. TPA cross section was calculated by Equation 1.

$$\delta = \delta_r(S_s\phi_s f_r c_r)/(S_r\phi_r f_s c_s) \qquad \text{[Equation 1]}$$

In Equation 1, s and r respectively stand for sample and reference molecules, S represents the intensity of a signal collected by the CCD detector, Φ represents the fluorescence quantum yield, f represents the overall fluorescence collection efficiency of the experimental apparatus, c represents molecular density in the solution, and $\delta_r$ represents the TPA cross section of reference molecules.

5) Cell Culturing

HeLa cells were cultured in Dulbecco's modified Eagle's medium (DMEM; Gibco) supplemented with heat-inactivated 10% (v/v) fetal bovine serum (FBS; Gibco), 100 units/mL penicillin and 100 μg/mL streptomycin. The cells were grown under a humidified environment at 37° C. with air/CO$_2$=95:5. Four days before imaging, the cells were harvested with a trypsin-EDTA solution and were transferred to a glass-bottomed dish (MatTek) with 50,000 cells/mm$^2$. The cells were treated at 37° C. for 20 minutes with 2 μM ANa1, and then loaded with 0.5 μM BCa1 at room temperature. 10 minutes later, the cells were imaged after washing 2 times with a reduced calcium-balanced salt solution (RCBSS; 127 mM NaCl, 3.8 mM KCl, 1.2 mM KH$_2$PO$_4$, 0.8 mM MgCl$_2$, 5 mM glucose and 10 mM HEPES buffer).

6) Two-Photon Fluorescence Microscopic Imaging

Two-photon fluorescence microscopic images of the probe-labeled HeLa cells and tissues were obtained using spectral confocal and multiphoton microscopes (Leica TCS SP2).

Figure 10:
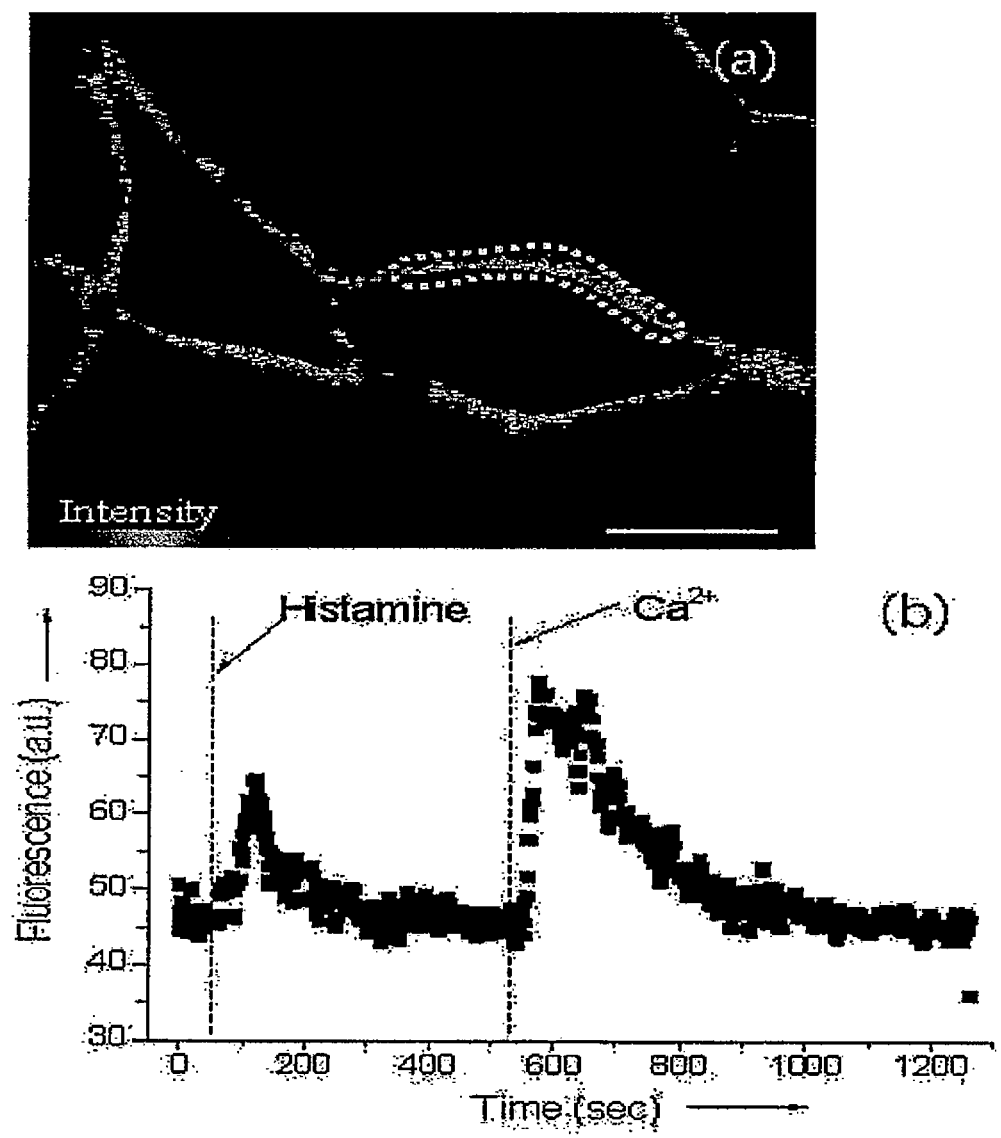
FIG. 10 (a) shows a TPM image of HeLa cells labeled with BCa1, and FIG. 10 (b) shows an analysis result thereof.

A TPM image of the HeLa cells labeled with BCa1 and an analysis result thereof are shown in FIG. 10.

Figure 11:
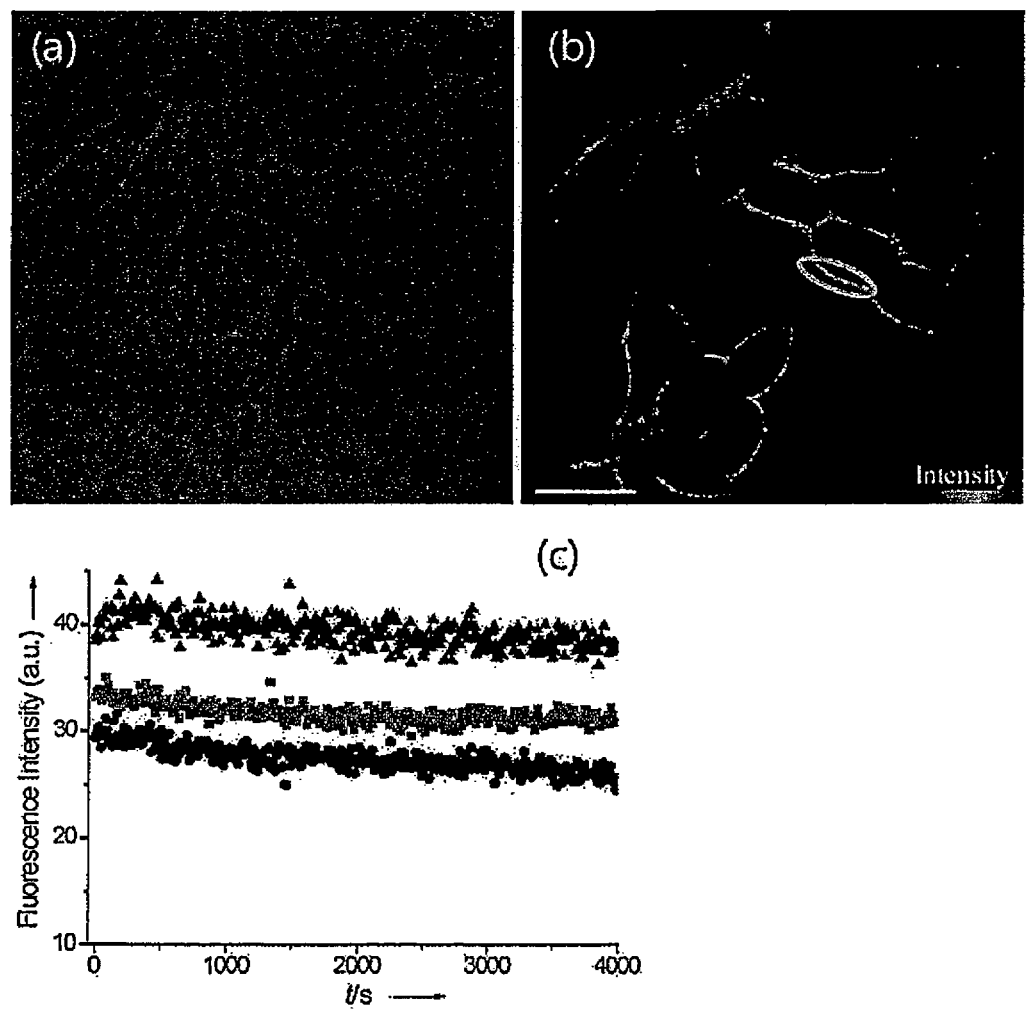
FIG. 11 shows an electron micrograph, a TPM image and fluorescence intensity of HeLa cells labeled with BCa1.

A bright-field image of the HeLa cells labeled with BCa1 (0.5 μM) collected at 390 to 450 nm (a), a TPM image (b), and relative TPEF intensity with time (c) are shown in FIG. 11.

Figure 12:
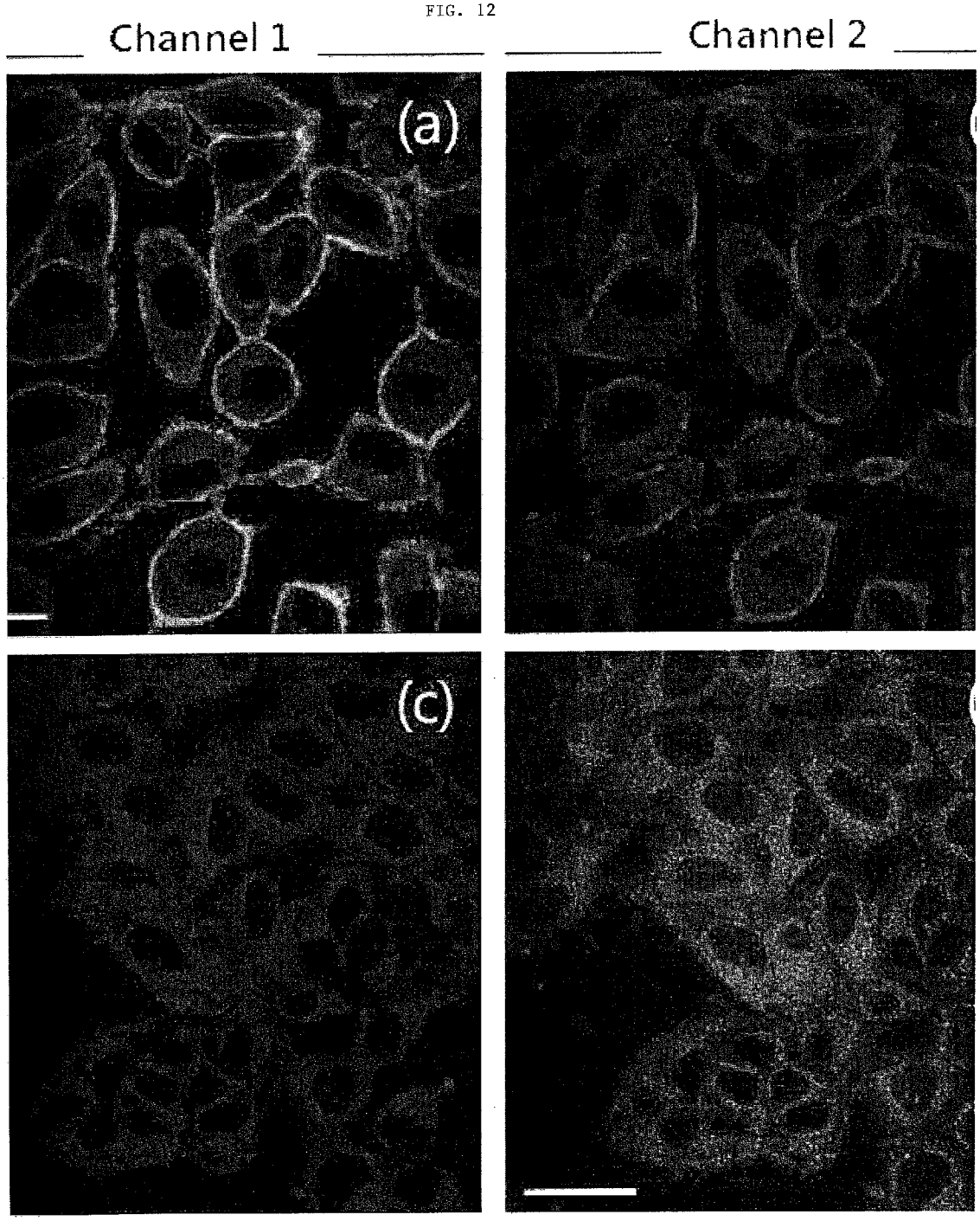
FIG. 12 shows TPM images of HeLa cells labeled with BCa1.

And, TPM images of HeLa cells labeled with 0.5 μM BCa1 and 2 μM ANa1 are shown in FIG. 12. More specifically, FIG. 12 (a) shows a TPM image of HeLa cells labeled with 0.5 μM BCa1 at 390 to 450 nm, FIG. 12 (b) shows a TPM image of HeLa cells labeled with 0.5 μM BCa1 at 500 to 560 nm, FIG. 12 (c) shows a TPM image of HeLa cells labeled with 2 μM ANa1 at 390 to 450 nm, and FIG. 12 (d) shows a TPM image of HeLa cells labeled with 2 μM ANa1 at 500 to 560 nm.

Figure 13:
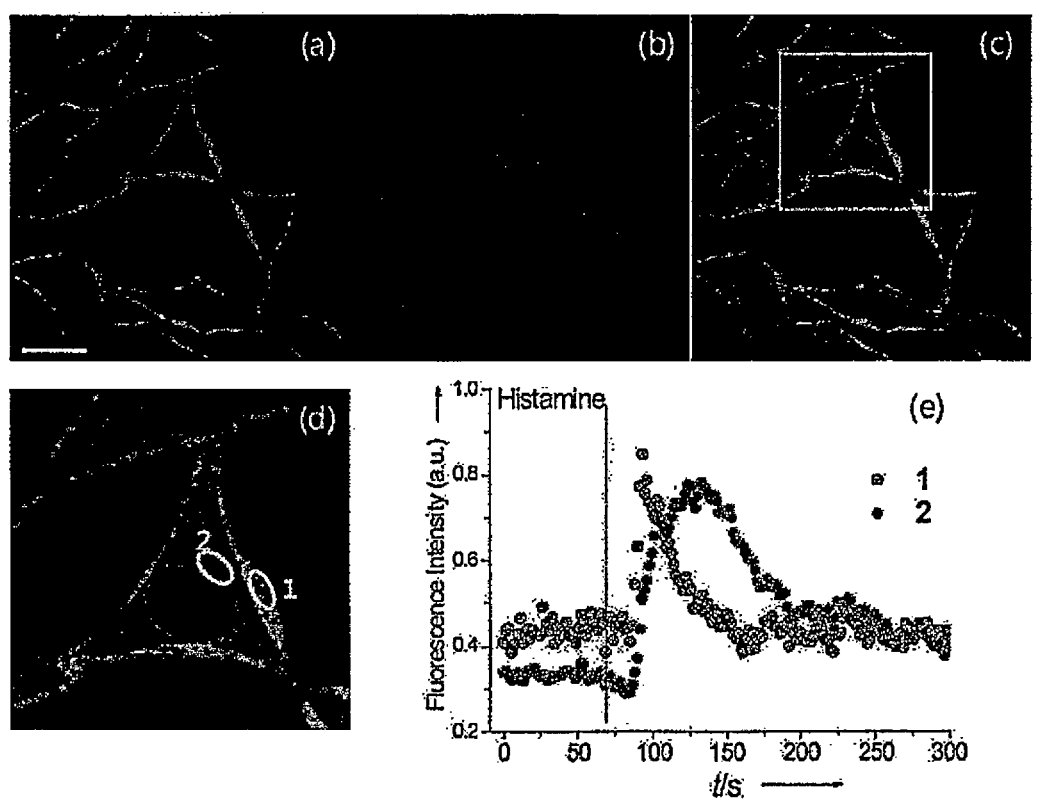
FIG. 13 shows TPM images and fluorescence intensity of HeLa cells labeled with BCa1 and ANa1.

TPM images and fluorescence intensity of HeLa cells labeled with BCa1 and ANa1 are shown in FIG. 13. More specifically, FIG. 13 (a) shows a TMP image of HeLa cells labeled with BCa1 at 390 to 450 nm, FIG. 13 (b) shows a TMP image of HeLa cells labeled with ANa1 at 500 to 560 nm, FIG. 13 (c) shows superimposition of (a) and (b), FIG. 13 (d) enlarges the box area in (c), and FIG. 13 (e) shows fluorescence intensity at the regions 1 and 2 in (d).

Thus, it can be seen that the change in $Na^+/Ca^{2+}$ can be monitored using a combination of BCa1 and ANa1.

7) Preparation Staining of Rat Hippocampal Slice

Hippocampal slices of a 2-week-old rat were prepared. Hippocampal tissue was cut into 400 μm-thick slices in an artificial cerebrospinal fluid (ACSF; 138.6 mM NaCl, 3.5 mM KCl, 21 mM $NaHCO_3$, 0.6 mM $NaH_2PO_4$, 9.9 mM D-glucose, 1 mM $CaCl_2$ and 3 mM $MgCl_2$) using a vibrating blade microtome. The slices were incubated with 10 mM BCa1 and 20 mM ANa1 in ACSF bubbled with 95& $O_2$ and 5% $CO_2$ at 37° C. for 40 minutes. Then, the slices were washed 3 times with ACSF, transferred to a glass-bottomed dish (MatTek), and observed under an electron microscope.

Figure 14:
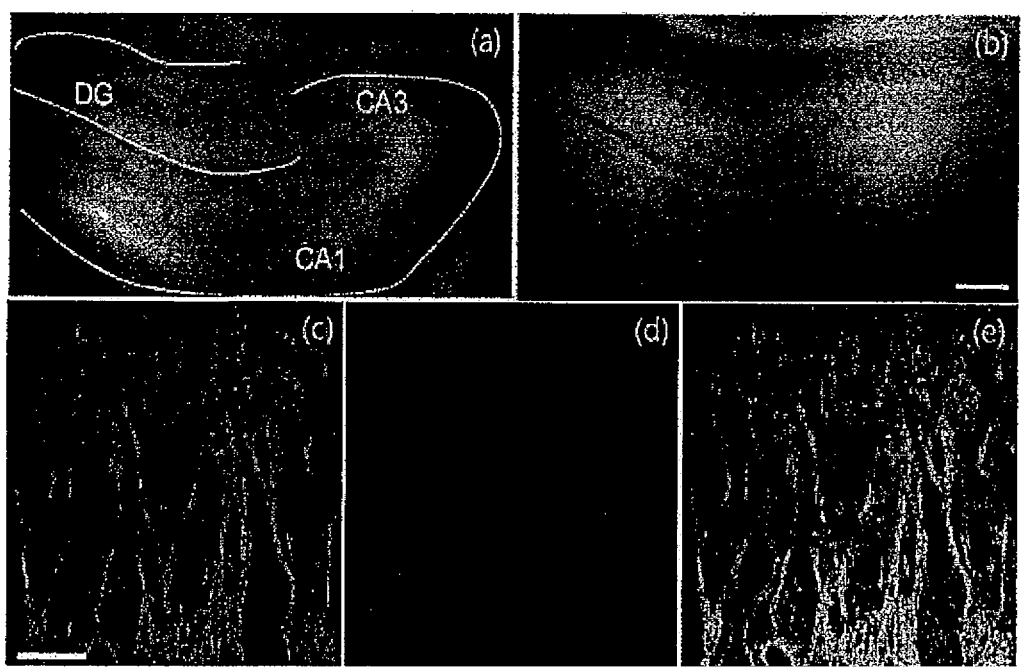
FIG. 14 shows images of a rat hippocampal slice stained with BCa1 and ANa1.

FIG. 14 shows images of the rat hippocampal slice stained with BCa1 and ANa1. More specifically, FIG. 14 (a) and (b) show a bright-field image of the CA1-CA3 regions as well as the TPM image dentate gyrus by 10× magnification and a TPM image. FIG. 14 (b) shows a 25 TPM image at 390 to 450 nm (channel 1) and 500 to 560 nm (channel 2). FIG. 14 (c) to (e) show TPM images of the CA3 region. (c) and (d) show TPM images of channel 1 and channel 2 at 100 to 200 μm depth, by 100× magnification, and (e) shows a superimposition thereof.

As described, the two-photon fluorescent probe for detecting calcium ions near the cell membrane according to the present disclosure reacts with calcium cations to exhibit strong two-photon fluorescence and may be selectively and easily loaded into the cell membrane by forming a complex with a calcium ion. Further, it allows imaging of the distribution of calcium cations in a living cell or tissue since it can selectively detect calcium ions in the living cell or tissue at a depth of 100 to 200 μm for more than 60 minutes, with a dissociation constant $K^t_d$ in cells of 78±5 μM. In addition, it allows simultaneous imaging of activities of calcium and sodium at different channels by staining the living cell or tissue with the two probes of different fluorescent color.

While the present disclosure has been described with respect to the specific embodiments, it will be apparent to those skilled in the art that various changes and modifications may be made without departing from the spirit and scope of the disclosure as defined in the following claims.

What is claimed is:

1. A two-photon fluorescent probe represented by Chemical Formula 1:

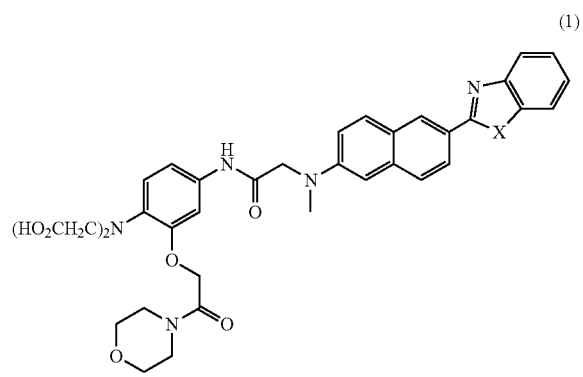

(1)

wherein X is O, S or NH.

2. The two-photon fluorescent probe according to claim 1, which reacts with a calcium ion to form a complex.

3. A two-photon fluorescent probe for detecting calcium ions in a living cell or tissue comprising a compound represented by Chemical Formula 1:

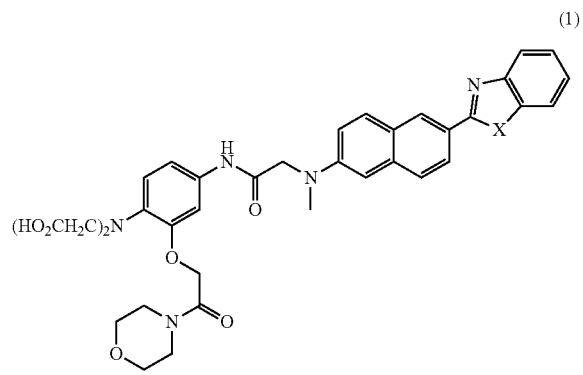

(1)

wherein X is O, S or NH.

4. A method for preparing a two-photon fluorescent probe represented by Chemical Formula 1 comprising:

refluxing a mixture of 6-bromo-N-methyl-2-naphthylamine, Proton-sponge and tert-butyl bromoacetate to prepare Compound B represented by Chemical Formula 2;

stirring a mixture of Compound B, benzoxazole, Pd(II)OAc, $PPh_3$, CuI and $CsCO_3$ to prepare Compound A represented by Chemical Formula 3; and mixing Compound A with 1-hydroxybenzotriazole and Compound D represented by Chemical Formula 4 and reacting the mixture:

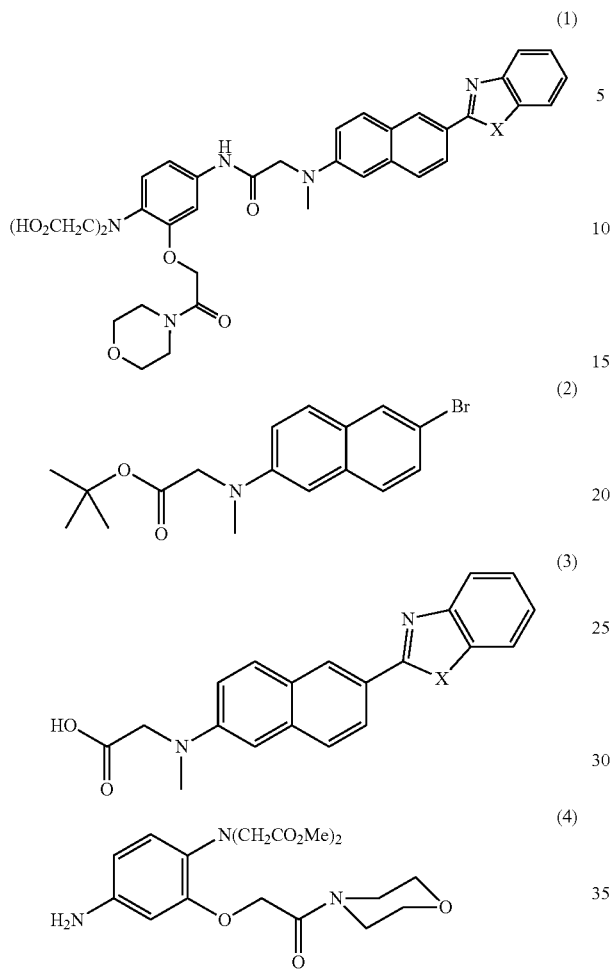

wherein X is O, S or NH.

5. A method for selectively imaging the distribution of calcium ions in a living cell or tissue using a two-photon fluorescent probe represented by Chemical Formula 1:

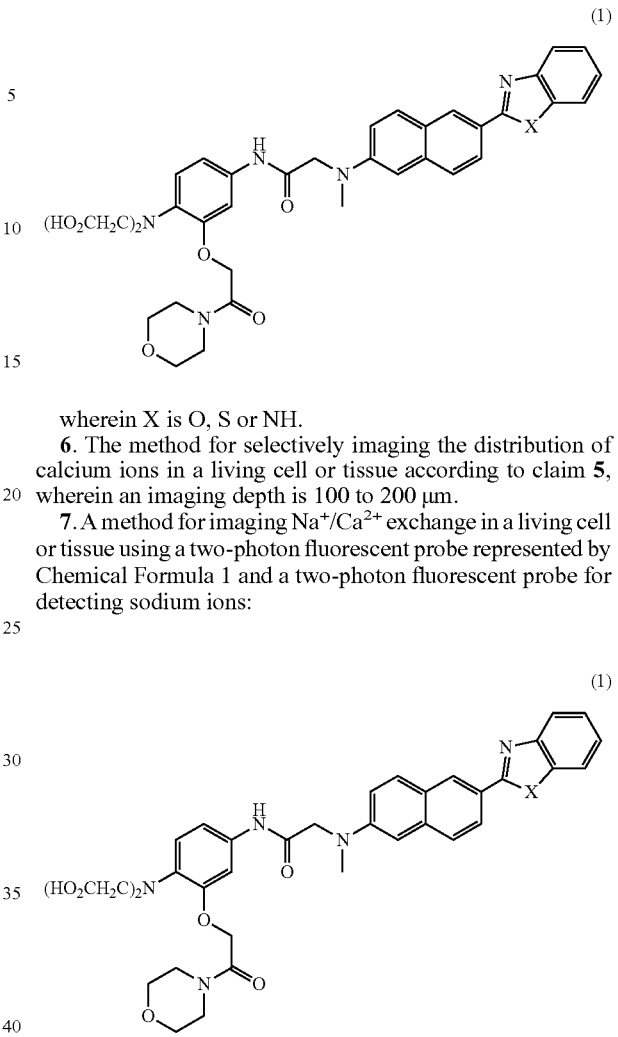

wherein X is O, S or NH.

6. The method for selectively imaging the distribution of calcium ions in a living cell or tissue according to claim 5, wherein an imaging depth is 100 to 200 μm.

7. A method for imaging $Na^+/Ca^{2+}$ exchange in a living cell or tissue using a two-photon fluorescent probe represented by Chemical Formula 1 and a two-photon fluorescent probe for detecting sodium ions:

wherein X is O, S or NH.

* * * * *